United States Patent [19]
Aster et al.

[11] Patent Number: 5,886,005
[45] Date of Patent: Mar. 23, 1999

[54] 4-AZA-19-NORANDROSTANE DERIVATIVES

[75] Inventors: Susan D. Aster, Teaneck; Donald W. Graham, Mountainside, both of N.J.

[73] Assignee: Merck & Co., Inc., Rahway, N.J.

[21] Appl. No.: 817,965

[22] PCT Filed: Jan. 12, 1996

[86] PCT No.: PCT/US96/00055

§ 371 Date: May 6, 1997

§ 102(e) Date: May 6, 1997

[87] PCT Pub. No.: WO96/22100

PCT Pub. Date: Jul. 25, 1996

Related U.S. Application Data

[63] Continuation-in-part of Ser. No. 373,341, Jan. 17, 1995, abandoned.

[51] Int. Cl.[6] .......................... A01N 43/42; C07D 221/02
[52] U.S. Cl. .............................. 514/284; 546/78; 546/77
[58] Field of Search ............................. 546/78; 514/284

[56] References Cited

U.S. PATENT DOCUMENTS

| | | | |
|---|---|---|---|
| 3,007,947 | 11/1961 | Counsell . | |
| 4,377,584 | 3/1983 | Rasmusson et al. | 546/77 |
| 4,684,635 | 8/1987 | Orentreich | 514/170 |
| 4,732,897 | 3/1988 | Cainelli et al. | 514/222 |
| 4,760,071 | 7/1988 | Rasmusson et al. | 514/284 |
| 4,859,681 | 8/1989 | Rasmusson et al. | 514/284 |
| 5,138,063 | 8/1992 | Rasmusson et al. | 546/77 |
| 5,510,351 | 4/1996 | Graham et al. | 514/284 |
| 5,510,485 | 4/1996 | Graham et al. | 514/284 |
| 5,512,555 | 4/1996 | Waldstreicher | 514/284 |
| 5,543,417 | 8/1996 | Waldstreicher | 514/284 |
| 5,578,599 | 11/1996 | Diani et al. | 514/289 |
| 5,719,158 | 2/1998 | Durette et al. | 546/78 |
| 5,739,137 | 4/1998 | Durette et al. | 546/78 |

FOREIGN PATENT DOCUMENTS

| | | |
|---|---|---|
| 0 004 949 | 10/1979 | European Pat. Off. . |
| WO 93/23048 | 11/1993 | WIPO . |
| WO 93/23050 | 11/1993 | WIPO . |
| WO 93/23051 | 11/1993 | WIPO . |

OTHER PUBLICATIONS

Jones et al., J. Med. Chem., 1993, vol. 36; pp. 421–423, Nonsteroidal inhibitors of human type 1 steroid 5alpha–reductase.

Frye et al., J. Med. Chem., 1993, vol. 36, pp. 4313–4315, "6–Azasteroids: Potent dual inhibitors of human type 1 and 2 steroid 5alpha–reductase".

Mellin et al., J. Steroid Biochem. Molec. Biol., vol. 44, pp. 121–131 (1993), "Azasteroids as inhibitors of testosterone 5alpha–reductase . . . ".

Rasmusson et al., J. Med. Chem., 1984, 27, pp. 1690–1701, "Azasteroids as inhibitors of rat prostatic 5alpha–reductase".

Rasmusson et al., J. Med. Chem., 1986, 29, pp. 2298–2315, "Azasteroids: Structure–activity relationships for inhibition of 5alpha–reductase and of androgen receptor binding".

Harris et al., Proc. Nat'l Acad. Sci., 1992, 89, pp. 10787–10791, "Identification and selective inhibition of an isozyme of steroid 5alpha–reductase in human scalp".

Diani et al., J. Clin. Endoc. & Metab., 74, 345–350 (1992), "Hair growth effects of oral administration of finasteride . . . ".

Helliker, Wall St. Journal, 7 Jun. 1991, pp. A1–A4, "Alopecia suffers seek to suffer less and not in silence".

Stinson, Chem. & Eng. News, 29 Jun. 1992, pp. 7–8, "Prostate drug Procar cleared for marketing".

Gormley et al., Chem. Abstract 118, 213352h (1992), "Prostatic cancer treatment involved combination therapy of a 5alpha–reductase inhibitor . . . ".

Gormley et al., Chem. Abstract 118, 102309e (1992), "A method of treating benign prostatic hyperplasia is claimed . . . ".

*Primary Examiner*—Donald G. Daus
*Attorney, Agent, or Firm*—Catherine D. Fitch; Melvin Winokur

[57] ABSTRACT

Compounds of the formula

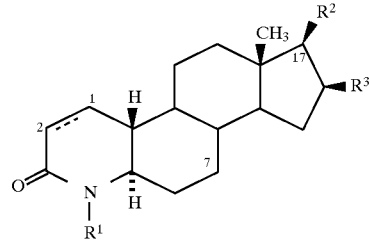

are inhibitors of 5α-reductase and are useful alone or in combination with other active agents for the treatment of hyperandrogenic disorders such as acne vulgaris, seborrhea, female hirsutism, male pattern baldness, and benign prostatic hyperplasia.

8 Claims, No Drawings

4-AZA-19-NORANDROSTANE DERIVATIVES

CROSS REFERENCE TO RELATED APPLICATIONS

The present application is the national phase application under 35 U.S.C. §371 of PCT application Ser. No. PCT/US96/00055, filed Jun. 16, 1996, which is a continuation-in-part of U.S. Ser. No. 08/373,341, filed Jan. 17, 1995.

FIELD OF THE INVENTION

The present invention provides novel compounds, novel compositions, methods of their use and methods of their manufacture, where such compounds are generally pharmacologically useful as agents in therapies whose mechanism of action rely on the inhibition of 5α-reductase, and more particularly, the inhibition of 5α-reductase isozyme type 1.

BACKGROUND OF THE INVENTION

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by an excessive accumulation of testosterone ("T") or similar androgenic hormones in the metabolic system. Androgenic alopecia is also known as androgenetic alopecia. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., *Endocrinol.* 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone ("DHT"), formed locally in the target organ by the action of 5α-reductase, which converts testosterone to DHT. Inhibitors of 5α-reductase will serve to prevent or lessen symptoms of hyperandrogenic stimulation in these organs. See especially U.S. Pat. Nos. 4,377,584, issued Mar. 22, 1983, and 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et al., *Proc. Natl. Acad. Sci. USA*, Vol. 89, pp. 10787–10791 (November 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

Since 5α-reductase type 1 and type 2 convert testosterone to DHT, inhibition of either or both of the isozymes would serve to alleviate the conditions and diseases mediated by DHT. The present invention addresses this by providing novel compounds that are active as inhibitors of 5α-reductase type 1.

SUMMARY OF THE INVENTION

The novel compounds of the present invention are those of structural formula I:

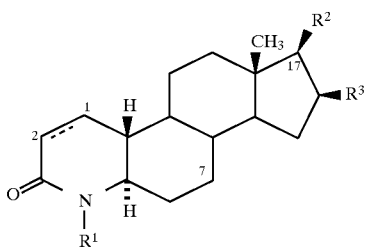

or a pharmaceutically acceptable salt or ester thereof, and are inhibitors of 5α-reductase, particularly 5α-reductase type 1. The compounds of formula I are useful in the oral, systemic, parenteral or topical treatment of hyperandrogenic conditions such as acne vulgaris, seborrhea, androgenic alopecia which includes female and male pattern baldness, female hirsutism, benign prostatic hyperplasia, and the treatment of prostatic carcinoma, as well as in the treatment of prostatitis.

Therefore it is an object of this invention to provide compounds that have sufficient activity in the inhibition of 5α-reductase type 1. It is an additional object of this invention to provide methods of using the compounds of formula I for the treatment of hyperandrogenic conditions such as acne vulgaris, seborrhea, androgenic alopecia, male pattern baldness, female hirsutism, benign prostatic hyperplasia, and the prevention and treatment of prostatic carcinoma, as well as the treatment of prostatitis. It is a further object of this invention to provide pharmaceutical compositions for the compounds of formula I. Another object of this invention is to provide compounds of formula I in combination with one or more other active agents, for example a 5α-reductase type 2 inhibitor, such as finasteride, a dual 5α-reductase type 1 and 2 inhibitor, a potassium channel opener such as minoxidil, an acne treatment such as retinoic acid or a derivative thereof, an anti-androgen such as flutamide, or an α1- or α1$_c$-adrenergic receptor antagonist, wherein such combinations would be useful in one or more of the above-mentioned methods of treatment or pharmaceutical compositions.

DETAILED DESCRIPTION OF THE INVENTION

The novel compounds of this invention have the structural formula I:

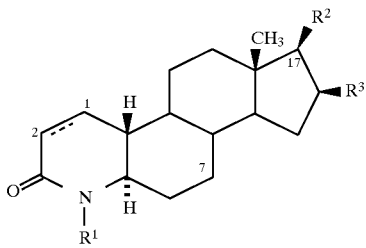

or a pharmaceutically acceptable salt or ester thereof, wherein: the C1–C2 bond designated "$\mathrm{---}$" represents a single or double bond;

$R^1$ is selected from —H, methyl and ethyl;

$R^2$ is selected from —H, —(CH2)$_n R^4$, —OCOR$^5$, and —OCON(R$^5$)2;

n is an integer selected from 1 to 6;

$R^3$ is —OR$^5$ when $R^2$ is —H, and $R^3$ is —H when $R^2$ is not —H;

$R^4$ is selected from —CN, —CON(R$^5$)$_2$, and —CO$_2$R$^5$; and $R^5$ is independently selected at each occurrence from:
a) —H,
b) —$C_{1-10}$ straight or branched chain alkyl,
c) —$C_{1-10}$ straight or branched chain alkyl substituted with 1 to 3 of phenyl, wherein each phenyl may independently be unsubstituted or substituted with 1 to 3 substituents selected from halo, —$CH_3$, —$OCH_3$, —$CF_3$ and —CN,
d) an aryl group selected from phenyl, naphthyl and biphenyl, wherein the aryl group may be unsubstituted or substituted with 1 to 3 substituents selected from halo, —$CH_3$, —$OCH_3$, —$CF_3$ and —CN, and
e) a heteroaryl group selected from pyridyl, pyrrolyl, thienyl, furanyl, quinolinyl, and thiazolyl.

Combinations of substituents and/or variables are permissable only if such combinations result in stable compounds.

Examples of compounds of this invention include, but are not limited to, the following:
17β-(2,2-dimethylpropionyloxy)-4-methyl-4-aza-5α-19-norandrostan-3-one;
17β-(4-methoxybenzoyloxy)-4-ethyl-4-aza-5α-19-norandrostan-3-one;
17β-pentanoyloxy-4-aza-5α-19-norandrost-1-ene-3-one;
17β-(t-butylaminocarbonyloxy)-4-methyl-4-aza-5α-19-norandrostan-3-one;
17β-(2-thiazolylaminocarbonyloxy)-4-aza-5α-19-norandrost-1-ene-3-one;
17β-(4-pyridylaminocarbonyloxy)-4-ethyl-4-aza-5α-19-norandrostan-3-one;
17β-(3-thienylaminocarbonyloxy)-4-aza-5α-19-norandrostan-3-one;
17β-dipropylaminocarbonyloxy-4-aza-5α-19-norandrost-1-ene-3-one;
21-cyano-4-methyl-4-aza-5α-19-norpregnan-3-one;
17βp-(5-cyanophenyl)-4-ethyl-4-aza-5α-19-norandrostan-3-one;
17β-(3-carboxypropyl)-4-aza-5α-19-norandrost-1-ene-3-one;
17β-(4-furanyloxycarbonylbutyl)-4-ethyl-4-aza-5α-19-norandrostan-3-one;
3-oxo-4-aza-5α-N-(2-naphthyl)-19-norpregnanamide;
3-oxo-4-methyl-4-aza-5α-N-(4-pyridyl)-19-norpregnanamide;
16p-(4-chlorophenoxy)-4-methyl-4-aza-5α-19-norandrostan-3-one;
16p-isopropoxy-4-aza-5α-19-norandrost-1-ene-3-one;
16-(3-pyrrolyloxy)-4-ethyl-4-aza-5α-19-norandrostan-3-one; and
16-decyloxy-4-aza-5α-19-norandrostan-3-one.

In one embodiment of the instant invention are compounds of formula I wherein the $C_1$–$C_2$ bond is a single bond and $R^1$ is —H or methyl.

In one class of this embodiment are compounds wherein $R^1$ is methyl; $R^2$ is —$OCOR^5$, —$OCONHR^5$ or —$(CH_2)_n R^4$; n is 1 or 2;
$R^4$ is —CN or —$CONHR^5$; and $R^5$ is selected from
a) —$C_{1-10}$ straight or branched chain alkyl,
b) —$C_{1-10}$ straight or branched chain alkyl substituted with 1 to 2 of phenyl, wherein each phenyl may independently be unsubstituted or substituted with 1 to 2 substituents selected from halo, —$CH_3$, —$OCH_3$, —$CF_3$ and —CN,
c) an aryl group selected from phenyl, naphthyl and biphenyl, wherein the aryl group may be unsubstituted or substituted with 1 to 2 substituents selected from halo, —$CH_3$, —$OCH_3$, —$CF_3$ and —CN, and
d) a heteroaryl group selected from pyridyl, pyrrolyl, thienyl, furanyl, quinolinyl, and thiazolyl.

Examples of compounds within this class include:
17β-(2,2-dimethylpropionyloxy)-4-methyl-4-aza-5α-19-norandrostan-3-one;
17β-(t-butylaminocarbonyloxy)-4-methyl-4-aza-5α-19-norandrostan-3-one;
21-cyano-4-methyl-4-aza-5α-19-norpregnan-3-one; and
3-oxo-4-methyl-4-aza-5α-N-(4-pyridyl)-19-norpregnanamide.

In a second class of this embodiment are compounds wherein $R^1$ is methyl; $R^2$ is —H; $R^3$ is $OR^5$; and $R^5$ is selected from
a) —$C_{1-10}$ straight or branched chain alkyl,
b) —$C_{1-10}$ straight or branched chain alkyl substituted with 1 to 2 of phenyl, wherein each phenyl may independently be unsubstituted or substituted with 1 to 2 substituents selected from halo, —$CH_3$, —$OCH_3$, —$CF_3$ and —CN,
c) an aryl group selected from phenyl, naphthyl and biphenyl, wherein the aryl group may be unsubstituted or substituted with 1 to 2 substituents selected from halo, —$CH_3$, —$OCH_3$, —$CF_3$ and —CN, and
d) a heteroaryl group selected from pyridyl, pyrrolyl, thienyl, furanyl, quinolinyl, and thiazolyl.

The compound 16β-(4-chlorophenoxy)-4-methyl-4-aza-5α-19-norandrostan-3-one is one example of a compound within this second class.

The term "Δ1" indicates a double bond at the C1–C2 position in formula I, and as such may be used throughout this application. For example, the name "16β-isopropoxy-4-aza-5α-19-norandrost-1-ene-3-one" and "Δ1-16β-isopropoxy-4-aza-5α-19-norandrostene-3-one" both refer to the same structural compound.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), secbutyl (s-Bu), tertbutyl (t-Bu), isopentane, isohexane, etc. "Alkenyl" is intended to include hydrocarbon groups of either a straight or branched configuration with one or more carbon-carbon double bonds which may occur in any stable point along the chain, such as ethenyl, propenyl or allyl, butenyl, pentenyl, and the like. Included in this invention are all E, Z diasteriomers. "Alkyloxy" (or "alkoxy") represents an alkyl group having the indicated number of carbon atoms attached through an oxygen bridge, e.g., methoxy, ethoxy, propyloxy, iso-propoxy, n-butoxy, iso-butoxy, sec-butoxy, t-butoxy and the like. "Halo" includes fluoro, chloro, bromo and iodo.

Also included within the scope of this invention are pharmaceutically acceptable salts of the compounds of fonnula I, where a basic or acidic group is present on the structure. Where a basic group is present, such as amino, an acidic salt, i.e. hydrochloride, hydrobromide, acetate, pamoate, and the like, can be used as the dosage form.

Representative salts include the following salts: acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, and valerate.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates and hydrates are encompassed within the scope of this invention.

The term "therapeutically effective amount" means that amount of a drug or pharmaceutical agent that will elicit the biological or medical response of a tissue, system, animal or human that is being sought by a researcher, veterinarian, medical doctor or other clinician, which includes alleviation of the symptoms of the disorder being treated. The novel methods of treatment of this invention are for disorders known to those skilled in the art. The term "mammal" includes humans.

The present invention has the objective of providing methods of treating hyperandrogenic conditions including acne vulgaris, seborrhea, female hirsutism and androgenic alopecia which includes male and female pattern baldness, by oral, systemic, parenteral or topical administration of the novel compounds of formula I either alone or in combination with one or more additional active ingredients such as a 5α-reductase 2 inhibitor, e.g. finasteride, a potassium channel opener, e.g. minoxidil, an anti-acne agent, e.g. retinoic acid, an anti-androgen, e.g. flutamide, and an α1 or α1$_c$ adrenergic receptor antagonist. The methods of treatment of this invention are intended to include the administration of a combination of a compound of formula I with a 5α-reductase 2 inhibitor and an additional active agent such as those noted above. The term "treating androgenic alopecia" is intended to include the arresting and/or reversing of androgenic alopecia, and the promotion of hair growth.

The present invention also has the objective of providing methods of treating benign prostatic hyperplasia, prostatitis, and treating prostatic carcinoma by oral, systemic or parenteral administration of the novel compounds of formula I either alone or in combination with a 5α-reductase 2 inhibitor, e.g. finasteride. Alternatively, treatment may encompass administration of a combination of a compound of formula I with a 5α-reductase 2 inhibitor and an additional active agent such as an α1 adrenergic receptor antagonist, e.g. terazosin or doxazosin, an α1$_c$ adrenergic receptor antagonist, or an anti-androgen, e.g. flutamide.

The present invention has the further objective of providing suitable topical, oral, systemic and parenteral pharmaceutical formulations for use in the novel methods of treatment of the present invention. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

The daily dosage of the products may be varied over a range from 0.01 to 1,000 mg per adult human/per day. For oral administration, the compositions are preferably provided in the form of tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg./kg. to about 50 mg./kg. of body weight per day. The range is more particularly from about 0.001 mg./kg. to 7 mg./kg. of body weight per day.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment of androgenic alopecia, male pattern baldness, acne vulgaris, seborrhea, and female hirsutism, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. These topical pharmaceutical compositions containing the compounds of the present invention ordinarily include about 0.005% to 5% by weight of the active compound in admixture with a pharmaceutically acceptable vehicle.

For the treatment of acne vulgaris, androgenic alopecia, male pattern baldness, seborrhea, female hirsutism, benign prostatic hyperplasia, prostatitis and the prevention and/or treatment of prostatic cancer, the compounds of the instant invention can be combined with a therapeutically effective amount of another 5α-reductase inhibitor, such as finasteride, or other 5α-reductase inhibitor compounds having type 2 inhibitory activity or dual inhibitory activity for both isozymes, in a single oral, systemic, or parenteral pharmaceutical dosage formulation. Alternatively, a combination therapy can be employed wherein the compound of formula I and the other 5α-reductase inhibitor are administered in separate oral, systemic, or parenteral dosage formulations. Also, for the skin and scalp related disorders of acne vulgaris, androgenic alopecia, seborrhea, and female hirsutism, the compounds of the instant invention and another 5α-reductase inhibitor such as finasteride can be formulated for topical administration. For example, a compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of formula I. See, e.g., U.S. Pat. No.'s 4,377,584 and 4,760,071 which describe dosages and formulations for 5α-reductase inhibitors.

Furthermore, administration of a compound of the present invention in combination with a therapeutically effective amount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, may be used for the treatment of androgenic alopecia including male pattern baldness. Therapy may further comprise the administration of a 5α-reductase type 2 inhibitor such as finasteride, or a 5α-reductase type 1 and type 2 dual inhibitor, in combination with a compound of the present invention and a potassium channel opener such as minoxidil. The active agents can be administered in a single topical dosage formulation, or each active agent can be administered in a separate dosage formulation, e.g., in separate topical dosage formulations, or an oral dosage formulation of a compound of formula I in combination with a topical dosage formulation of, e.g., minoxidil, or a single oral dosage formulation of a compound of formula I and another 5α-reductase inhibitor, in combination with a topical dosage formulation of, e.g., minoxidil. See, e.g., U.S. Pat. No. 's 4,596,812, 4,139,619 and WO 92/02225, published 20 Feb. 1992, for dosages and formulations of calcium channel openers.

Furthermore, for the treatment of acne vulgaris, a combined therapy can be used by administering a therapeutically effective amount of a compound of formula I in combination with a therapeutically effective amount of retinoic acid or a derivative thereof, e.g. an ester or amide derivative thereof, such as e.g., tretinoin or isotretinoin. Optionally, this combined therapy for acne vulgaris may further include a 5α-reductase type 2 inhibitor such as finasteride, or a dual 5α-reductase type 1 and 2 inhibitory compound.

Also, for the treatment of benign prostatic hyperplasia, a combined therapy comprising a administration of a compound of formula I with a 5α-reductase type 2 inhibitor, such as e.g., finasteride, and an alpha-1 adrenergic receptor antagonist, such as e.g., terazosin, doxazosin, prazosin, bunazosin, indoramin or alfuzosin, may be employed. More particularly, the combined therapy can comprise administering a compound of formula I with a 5α-reductase type 2 inhibitor, such as e.g., finasteride, and an alpha-$1_c$ adrenergic receptor antagonist. Compounds which are useful as alpha-$1_c$ adrenergic receptor antagonists can be identified according to the procedures described in PCT/US93/09187 (WO94/08040, published Apr. 14, 1994)issued as U.S. Pat. Nos. 5,556,753 and 5,714,381; PCT/US94/03852 (WO 94/22829, published Oct. 13, 1994), PCT/US94/10162 (WO 95/07075, published Mar. 16, 1995); and U.S. Pat. No. 5,403,847.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantion, glycerine, vitamin A and E oils, mineral oil, PPG2 myristyl propionate, and the like, to form, e.g., alcoholic solutions., topical cleansers, cleansing creams, skin gels, skin lotions, and shampoos in cream or gel formnulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

SCHEME I

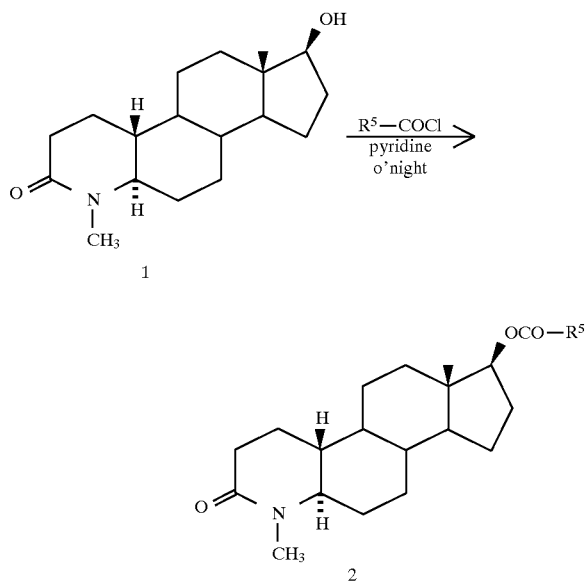

The starting material (1) is known in the art and its preparation described in G. Rasmusson et al, *J. Med. Chem.*, 1984, 27, p. 1694, Table II, no. 4ee. Compound (1) is treated in pyridine with an acid chloride such as pivaloyl chloride at room temperature to give the corresponding ester (2).

Other acid chlorides ($R^5COCl$) where $R^5$ could be methyl, ethyl, isopropyl, tert-butyl, isodecyl, phenyl, p-chlorophenyl, biphenyl, pyridyl, thienyl may be used as well. Alternatively, the corresponding carboxylic acid may be used with an ester forming reagent such as dicyclohexylcarbidiimide or 1-(3-dimethylaminopropyl)-3-ethylcarbodiimide hydrochloride to form compounds of formula (2).

For compounds where $R^1$ is H, the seco acid used to prepare (1) can be treated with ammonium acetate rather than methylamine hydrochloride-sodium acetate which will ultimately give the 4-H analog of ester (2); where $R^1$ is ethyl, ethylamine hydrochloride may be used instead.

The above 4-H analog of ester (2) can be reacted with 2,3-dichloro-5,6-dicyanobenzoquinone using the procedure of Dolling et al, *J. Amer. Chem. Soc.*, 1988, 110, 3318–3319, to give the $\Delta^1$-4-H analog of ester (2).

SCHEME II

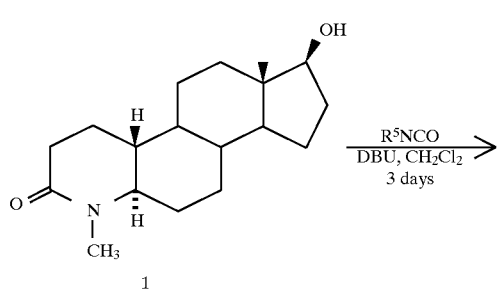

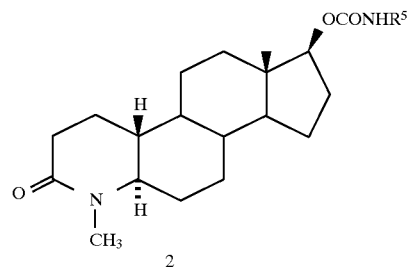

As depicted in Scheme II, compound (1) is treated with an isocyanate such as t-butyl isocyanate in methylene chloride in the presence of 1,8-diazabicyclo[5.4.0]-undec-7-ene (DBU) at room temperature to give the carbamate (3).

Other isocyanates ($R^5NCO$) where $R^5$ could be methyl, ethyl, isopropyl, isodecyl, phenyl, p-chlorophenyl, biphenyl, pyridyl or thienyl, may be used as well. Compound (3) where $R^5$ is —H is obtained by reacting (1) with acetic acid/NaOCN. N-di-substituted analogs can be made by treating (1) with reagents of the formula $ClC(O)N(R^5)_2$, which are commercially available.

SCHEME III

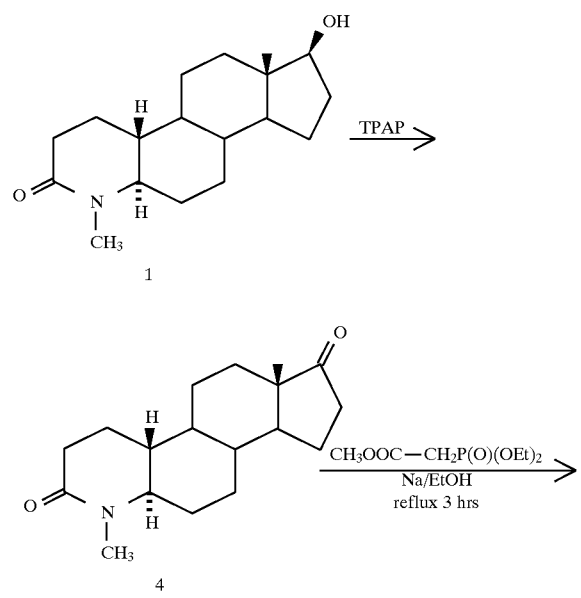

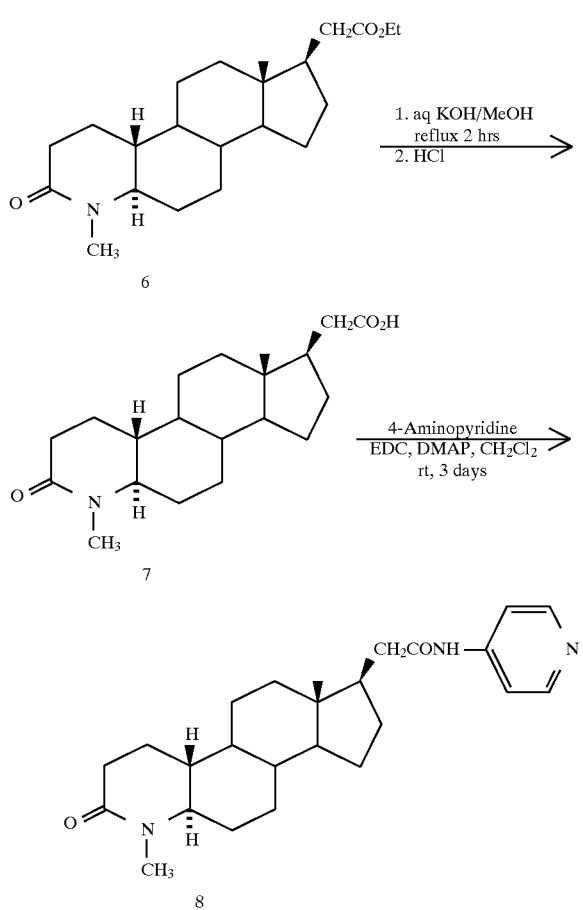

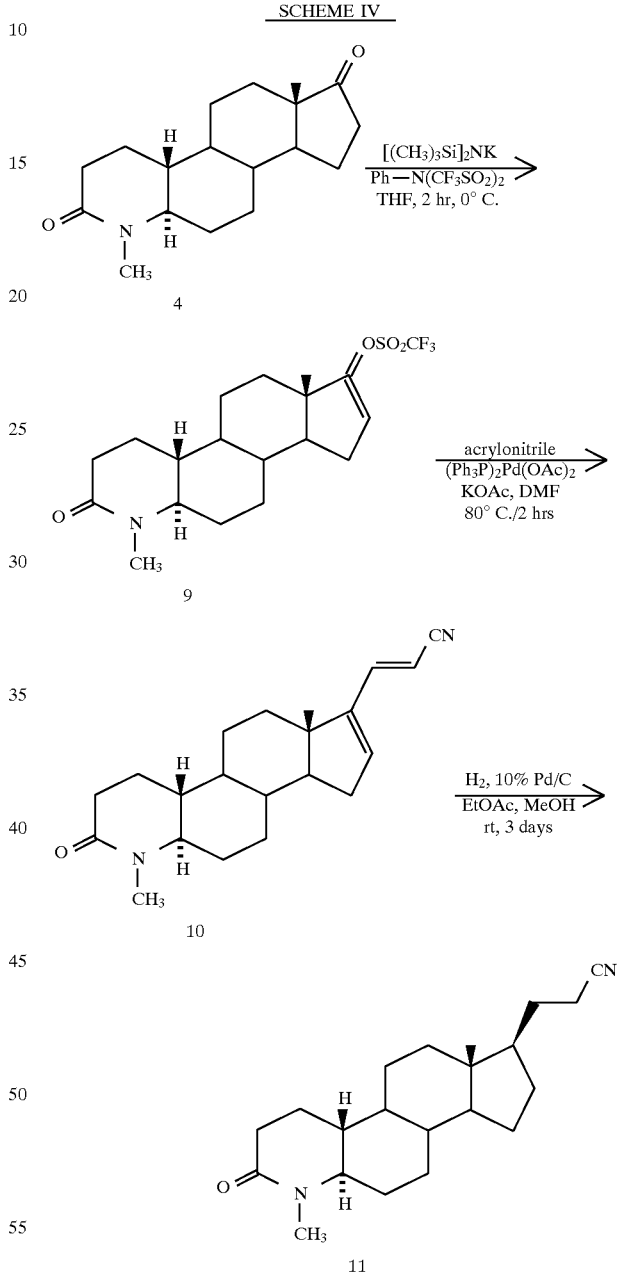

As shown in Scheme III, compound (1) is oxidized to the ketone (4) with a catalytic amount of tetrapropylammonium perruthenate(VII) (TPAP), in the presence of N-methylmorpholine-N-oxide and 4 Å molecular sieves in methylene chloride. The resulting ketone (4) is treated under Wittig conditions with methyl diethylphosphonoacetate and a strong base such as sodium in ethanol to give the unsaturated ethyl ester (5). Alternatively, sodium in methanol could be used instead to give the methyl ester. The 17-olefin is then reduced to the saturated ester (6) by hydrogenating with palladium hydroxide as the catalyst. Other catalyts including palladium on carbon, palladium or platinum alone also may be used. The ethyl ester (6) is saponified using a base such as KOH, although other bases such as NaOH and LiOH may also be employed. The resulting carboxylic acid (7) is reacted with 4-aminopyridine in the presence of 1-(3-dimethyl-aminopropyl)-3-ethylcarbodiimide hydrochloride (EDC) and a catalyst such as 4-dimethylaminopyridine (DMAP) to give the amide (8). Reaction of carboxylic acid (7) with other amines such as NH$_3$, diethylamine, methylamine, dimethylamine, dioctylamine, tert-butylamine, aniline, p-chloroaniline, 2-aminopyridine, 4-amino-biphenyl, benzylamine, diphenylmethylamine, 2-aminothiazole, 2-aminofuran, 2-aminoquinoline or the like with EDC or other common amide forming reagents such as dicyclohexylcarbodiimide or N,N-bis[2-oxo-3-oxazolinidyl]-phosphorinic acid will give the corresponding amides.

When $R^4$ is $CO_2R^5$, the carboxylic acid (7) could be reacted with an alcohol such as tert-butanol, isopropanol, n-hexanol, phenol, 2-methoxyphenol, 2-hydroxypyridine, or 2-hydroxyquinoline using an ester forming reagent such as dicyclohexylcarbodiimide or 1-(3-dimethylaminopropyl)-3-ethylcarbodiimide hydrochloride. Alternatively, the carboxylic acid (7) can be converted into the acid chloride with thionyl chloride or oxalyl chloride, and the acid chloride reacted with the appropriate alcohol in the presence of a catalyst such as 4-dimethylaminopyridine.

As shown in Scheme IV, compound (4) is treated with potassium bis(trimethylsilyl)-amide and N-phenyltrifluoromethanesulfonimide to form the 17-enoltriflate (9). The triflate (9) is treated with an olefin such as acrylonitrile in the presence of a catalytic amount of bis(triphenyl-phosphine)palladium(II)acetate and potassium acetate in dimethylformamide (DMF) to yield the cyanodiene (10). The diene is then reduced to the saturated nitrile (11) hydrogenating with palladium on carbon in an ethyl acetate-methanol solvent mixture.

For compounds where R² is (CH₂)ₙR⁴ and R⁴ is CN, the enoltriflate (9) can be treated with other olefins such as allyl nitrile, 4-cyano-1-butene or 5-cyano-1-pentene and the like using the catalyst above. To prepare compounds where R⁴ is CO₂H, the enoltriflate can be reacted with substituted acetylenes such as 3-butynoic acid or 4-pentynoic acid in the presence of the catalyst above and CuI plus diisopropyl amine. Amides and esters can then be made from the acid (where R⁴ is CO₂H) using standard procedures known in the art.

SCHEME V

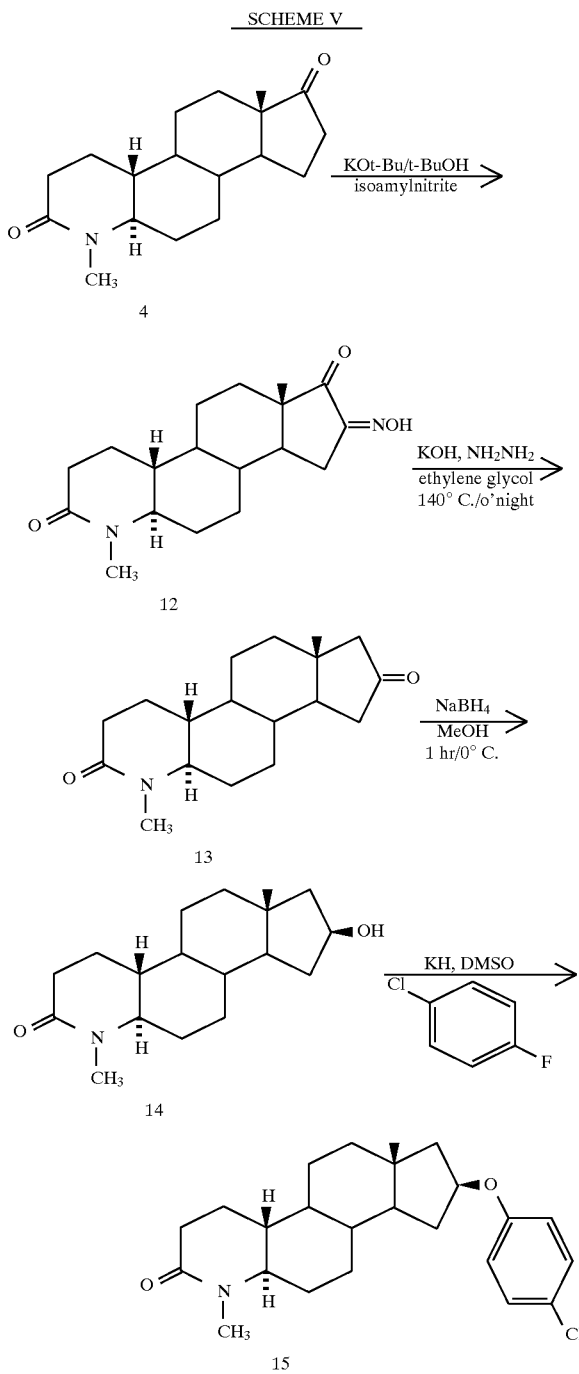

As shown in Scheme V, compound (4) is treated with isoamyl nitrite in the presence of potassium tert-butoxide in tert-butanol to give (12), the 17-ketone-16-oxime. The oxime is heated under Wolff-Kishner conditions with hydrazine and KOH in ethylene glycol, to give (13) the 16-ketone. The ketone (13) is reduced to give the alcohol (14) using NaBH₄ in methanol although lithium tri-tert-butoxyyaluminohydride in tetrahydrofuran (THF) may be used as well. The alcohol is then reacted with 4-chlorofluorobenzene in the presence of KH in dimethylsulfoxide (DMSO) to give the ether (15).

Other ethers, (OR⁵), may be prepared by using the corresponding alkylbromides such as methyl-, ethyl-, isopropyl-, tert-butyl-, or isodecylbromide or the corresponding arylfluorides such as phenyl-, 4-methoxyphenyl-, biphenyl-, or 4-pyridylfluoride.

The following non-limiting Examples are presented to further illustrate the invention. The NMR data was obtained using CDCl₃ at 400 MHz.

EXAMPLE 1

Preparation of 17β-(2,2-dimethylpropionyloxy)-4-methyl-4-aza-5α-19-norandrostan-3-one (2)

To a solution of 17β-hydroxy-4-methyl-4-aza-5α-19-norandrostan-3-one (1) (60 mg, 0.206 mmoles) in pyridine (1 ml) in a N₂ atmosphere was added pivaloyl chloride (101 μl, 0.823 mmoles) and the resulting solution stirred at room temperature for 18 hours. The reaction mixture was diluted with methylene chloride (10 ml) and washed with 1N HCl (2 times), H₂O, brine and dried over MgSO₄. Evaporation in vacuo and flash chromatography on silica gel with 6:1 chloroform-acetone gave 2 as a white solid. NMR (CDCl₃): δ 0.82 (s, 3H, 18-Me); 1.18 (s, 9H, Me₃C); 2.89 (dd, 1H, 5-H); 2.90 (s, 3H, 4-Me); 4.55 (t, 1H, 17-H).

EXAMPLE 2

Preparation of 17β-(t-butylaminocarbonyloxy)-4-methyl-4-aza-5α-19-norandrostan-3-one (3)

To a solution of 17β-hydroxy-4-methyl-4-aza-5α-19-norandrostan-3-one (1) (60 mg, 0.206 mmoles) in methylene chloride (1 ml), in a N₂ atmosphere was added t-butyl isocyanate (97 μl, 0.824 mmoles) and 1,8-diazabicyclo [5.4.0]-undec-7-ene (123 μl, 0.824 mmole). After stirring at room temperature for 3 days, the reaction mixture was diluted with methylene chloride (10 ml) and washed with 1N HCl, H₂O, brine and dried over MgSO₄. Evaporation in vacuo and flash chromatography on silica gel with 4:1 methylene chloride-acetone followed by recrystallization from ethyl acetate gave 3 as a white solid. NMR(CDCl₃): δ 0.79 (s, 3H, 18-Me); 1.31 s, 9H, Me3C); 2.90 (dd, 1H, 5-H); 2.92 (s, 3H, 4-Me); 4.50 (t, 1H, 17-H); 4.59 (s, 1H, N-H).

EXAMPLE 3

Preparation of 4-methyl-4-aza-5α-19-norandrostan-3,17-dione (4)

To a mixture of 17β-hydroxy-4-methyl-4-aza-5α-19-norandrostan-3-one (1) (1.64 g, 5.63 mmoles), N-methylmorpholine-N-oxide (1.02 g, 8.45 mmoles)., and 3 g 4Å powdered molecular sieves in methylene chloride (12 ml) was added tetrapropylammonium perruthenate(VII) (102 mg, 0.282 mmoles). After stirring for 3 minutes, a short (30 second) exotherm ensued and the mixture was stirred for 1 hour at room temperature. The reaction mixture was filtered through several inches of tlc grade silica gel with ethyl acetate. The filtrate was washed with 1N HCl, H₂O, brine and dried over MgSO₄. Evaporation in vacuo gave 4 as a white solid. NMR (CDCl₃): δ 0.90 (s, 3H, 18-Me); 2.90 (dd, 1H, 5-H); 2.95 (s, 3H, 4-Me).

EXAMPLE 4

Preparation of ethyl 3-oxo-4-methyl-4-aza-5α-19-norpregn-17,20-enoate (5)

To an ethanol solution of sodium ethoxide prepared by dissolving sodium (120 mg, 5.22 mmoles) in ethanol (2 ml) in a $N_2$ atmosphere was added 4-methyl-4-aza-5α-19-norandrostane-3,17-dione (4) (471 mg, 1.63 mmoles) and methyl diethylphosphonoacetate (935 μl, 4.89 mmoles) and the resulting solution heated under reflux for 3 hours. The cooled mixture was evaporated in vacuo and the residue partitioned with methylene chloride-1N HCl. The organic phase was washed with $H_2O$, 5% $NaHCO_3$, brine and dried over $MgSO_4$. After evaporation in vacuo the residue was triturated with warm diethyl ether, cooled and filtered to give 5 as a white solid. NMR ($CDCl_3$): δ 0.85 (s,3H, 18-Me); 1.29 (t, 3H, $OCH_2CH_3$); 2.90 (dd, 1H, 5-H); 2.92 (s, 3H, 4-Me); 4.18 (q, 2H, $OCH_2$); 5.53 (m, 1H, 20-H).

EXAMPLE 5

Preparation of ethyl 3-oxo-4-methyl-4-aza-5α-19-norpregnanoate (6)

Ethyl 3-oxo-4-methyl-4-aza-5α-19-norpregn-17,20-enoate (5) (443 mg, 1.23 mmoles) was hydrogenated at atmospheric pressure and room temperature with palladium hydroxide (80 mg) in ethanol (7 ml). After 24 hours the catalyst was filtered and washed with ethanol. Evaporation in vacuo of the filtrate gave 6 as a crystalline solid. NMR ($CDCl_3$): 0.61 (s, 3H, 18-Me); 1.25 (t, 3H, $OCH_2CH_3$); 2.90 (dd, 1H, 5-H); 2.91 (s,3H, 4-Me); 4.12 (q, 2H, $OCH_2$).

EXAMPLE 6

Preparation of 3-oxo-4-methyl-4-aza-5α-19-norpregnanoic acid (7)

A mixture of ethyl 3-oxo-4-methyl-4-aza-5α-19-norpregnanoate (6) (445 mg, 1.23 mmoles) and 9M KOH (410 μl 3.69 mmoles) in methanol (4 ml) was heated under reflux for 2 hours. The cooled solution was evaporated in vacuo and the residue dissolved in $H_2O$. The solution was acidified with concentrated HCl and the mixture extracted with methylene chloride (3 times). The combined extracts were washed with brine and dried over MgSO4. Evaporation in vacuo gave 7 as a white solid. NMR ($CDCl_3$): δ 0.63 (s, 3H, 18-Me); 2.91 (dd, 1H, 5-H); 2.93 (s, 3H, 4-Me).

EXAMPLE 7

Preparation of 3-oxo-4-methyl-4-aza-5α-N-(4-pyridyl)-19-norpregnanamide (8)

A mixture of 3-oxo-4-methyl-4-aza-5α-19-norpregnanoic acid (7) (80 mg, 0.240 mmoles), 4-aminopyridine (28 mg, 0.288 mmoles), 1-(3-dimethylaminopropyl)-3-ethylcarbodiimide hydrochloride (64 mg, 0.336 mmoles) and 4-dimethylaminopyridine (5 mg) in methylene chloride (5 ml) was stirred at room temperature for 3 days. The reaction mixture was washed with brine and dried over $MgSO_4$. Evaporation in vacuo and purification by preparative thin layer chromatography on silica gel with 10% methanol in methylene chloride gave 8 as a white solid. NMR ($CDCl_3$) δ 0.65 (s, 3H, 18-Me); 2.90 (dd, 1H, 5-H); 2.92 (s, 3H, 4-Me); 7.49 (d, 2H, ArH); 7.89 (s, 1H, N-H); 8.48 (d, 2H, ArH).

EXAMPLE 8

Preparation of 17-trifluomethylsulfonyloxy-4-methyl-4-aza-5α-19-norandrost-16-ene-3-one (9)

To a partial solution of 4-methyl-4-aza-5α-19-norandrostan-3,17-dione (4) (1 g, 3.46 mmoles) in tetrahydrofuran (7 ml) cooled in an ice bath in a $N_2$ atmosphere was added potassium bis(trimethylsilyl)amide (0.5M in toluene, 7.6 ml, 3.81 mmole) and the resulting mixture stirred at 0° C. for 1 hour. N-phenyltrifluomethanesulfonimide (1.48 g, 4.15 mmoles) was added and the reaction mix stirred at 020 C. for 1 hour. The mixture was diluted with $H_2O$, extracted with ethyl acetate, and dried over $MgSO_4$. Evaporation in vacuo and flash chromatography on silica gel with 4:1 hexane-isopropanol gave 9 as a white solid. NMR ($CDCl_3$): δ 1.01 (s, 3H, 18-Me); 2.90 (dd, 1H, 5-H); 2.94 (s, 3H, 4-Me); 5.60 (m, 1H, 16-H).

EXAMPLE 9

Preparation of 21-cyano-4-methyl-4-aza-5α-19-norpregn-16,20-diene-3-one (10)

A mixture of 17-trifluomethylsulfonyloxy-4-methyl-4-aza-5α-19-norandrost-16-ene-3-one (9) (150 mg, 0.356 mmoles), acrylonitrile (94 μl, 1.42 mmoles), potassium acetate (139 mg, 1.42 mmoles) and bis(triphenylphosphine)palladium(II)acetate (27 mg, 0.0356 mmoles) in DMF (3 ml) was heated at 80° C. for 2 hours in a $N_2$ atmosphere. The cooled readtion mixture was diluted with methylene chloride and washed with $H_{20}$, brine and dried over $MgSO_4$. Evaporation in vacuo and flash chromatography on silica gel with 4:1 hexane-isopropanol gave (10) as a white solid and as a mixture of cis-trans isomers. NMR ($CDCl_3$): δ 0.84 (s, .63H, 18-Me);0.93 (s, 2.37H, 18-Me); 2.90 (dd, 1H, 5-H); 2.93 (s, 3H, 4-Me); 5.25–7.00 (m, 3H, 16-H, 20-H, 21-H).

EXAMPLE 10

Preparation of 21-cyano-4-inethyl-4-aza-5α-19-norpregnan-3-one (II)

21-Cyano-4-methyl-4-aza-5α-9-norpregn-16,20-diene-3-one (10) (71 mg, 0.219 mmoles) was hydrogenated at atmospheric pressure and room temperature with 10% palladium on carbon (25 mg) in ethyl acetate (4 ml) and methanol (0.5 ml). After 3 days, the catalyst was filtered and washed with methanol. Evaporation of the filtrate in vacuo and flash chromatography on silica gel with 4:1 hexaneisopropanol gave 11 as a white solid. NMR ($CDCl_3$): d 0.63 (s, 3H, 18-Me); 2.90 (dd, 1H, 5-H); 2.02 (s, 3H, 4-Me).

EXAMPLE 11

Preparation of 4-methyl-4-aza-5α-19-norandrostan-16-oxime-3,17-dione (12)

A mixture of potassium t-butoxide (219 mg, 1.97 mmoles) in t-butanol (4.5 ml) and 4-methyl-4-aza-5α-19-norandrostan-3,17-dione (4) (285 mg, 0.986 mmoles) was stirred at room temperature in a $N_2$ atmosphere for 1 hour. Isoamyl nitrite (263 μl, 1.97 mmoles) was added and after stirring at room temperature for 18 hours, the mixture was diluted with $H_2O$, acidified with concentrated HCl and extracted with methylene chloride (2 times) and with ethyl acetate (2 times). Some crude product was obtained by filtration of the aqueous phase. The combined organic phases were washed with brine and dried over $MgSO_4$. Evaporation in vacuo and purification of this residue plus the crude product above by flash chromatography on silica gel with 2%–5% methanol in methylene chloride gave 12 as a white solid. NMR (CDCl$_3$): δ 1.00 (s, 3H, 18-Me); 2.90 (dd,1H, 5-H); 2.92 (s,3H, 4-Me).

EXAMPLE 12

Preparation of 4-methyl-4-aza-5α-19-norandrostan-3,16-dione (13)

A mixture of 4-methyl-4-aza-5α-19-norandrostan-16-oxime-3,17-dione (12) (132 mg, 0.415 mmoles), anhydrous hydrazine (15 μl, 0.457 mmoles) and powdered potassium hydroxide (139 mg, 2.49 mmoles) in ethylene glycol (1.5 ml) was heated at 140° C. in a N$_2$ atmosphere with magnetic stirring for 18 hours. The cooled reaction mixture was diluted with H$_2$O, acidified with concentrated HCl and extracted with methylene chloride (3 times). The combined extracts were washed with brine and dried over MgSO$_4$. Evaporation in vacuo and flash chromatography on silica gel with 3% methanol in methylene chloride gave 13 as a white solid. NMR (CDCl$_3$): δ 0.92 (s, 3H, 18-Me); 2.90 (dd, 1H, 5-H);. 2.92 (s, 3H, 4-Me).

EXAMPLE 13

Preparation of 16β-hydroxy-4-methyl-4-aza-5α-19-norandrostan-3-one 14)

A mixture of 4-methyl-4-aza-5α-19-norandrostan-3,16-dione (13) (33 mg, 0.114 mmoles) and sodium borohydride (13 mg, 0.342 mmoles) in methanol (0.75 ml) was stirred at 0° C. in a N$_2$ atmosphere for 1 hour. The mixture was acidified with concentrated HCl and extracted with methylene chloride (3 times). The combined extracts were washed with brine, dried over MgSO$_4$ and evaporated in vacuo to give 14 as a white solid. NMR (CDCl$_3$): δ 0.95 (s, 3H, 18-Me); 2.86 (dd,1H, 5-H); 2.91 (s, 3H, 4-Me); 4.38 (m, 1H, 16-H).

EXAMPLE 14

Preparation of 16β-(4-chlorophenoxy)-4-methyl-4-aza-5α-19-norandrostan-3-one (15)

A mixture of 16β-hydroxy-4-methyl-4-aza-5α-19-norandrostan-3-one (14) (17 mg, 0.058 mmoles) and 35% potassium hydride in mineral oil (13 mg, 0.117 mmoles) in dimethylsulfoxide (0.2 ml) was stirred at room temperature in a N$_2$ atmosphere for 20 minutes. 1-Chloro-4-fluorobenzene was added and the mixture stirred at room temperature for 18 hours. Saturated ammonium chloride solution (2 drops) was added to the cooled mixture which was then extracted with methylene chloride. The extract was washed with H$_2$O, brine and dried over MgSO$_4$. Evaporation in vacuo and purification by preparative thin layer chromatography on silica gel with 5% methanolmethylene chloride gave 15 as a white solid. NMR (CDCl$_3$): δ 0.95 (s, 3H, 18-Me); 2.89 (dd, 1H, 5-H); 2.92 (s, 3H, 4-Me); 4.70 )m, 1H, 16-H); 6.73 (d, 2H, ArH); 7.18 (d, 2H, ArH).

Biological Assays
Preparation of Human Prostatic and Scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase Assay

The reaction mixture for the type 1 5α-reductase contained 40 mM potassium phosphate, pH 6.5, 5 mM [7-$^3$H]-testosterone, 1 mM dithiothreitol and 500 μM NADPH in a final volume of 100 μl. The reaction mixture for the type 2 5α-reductase contained 40 mM sodium citrate, pH 5.5, 0.3 mM [7-$^3$H]-testosterone, 1 mM dithiothreitol and 500 μM NADPH in a final volume of 100 μl. Typically, the assay was initiated by the addition of 50–100 μg prostatic homogenate or 75–200 μg scalp homogenate and incubated at 37° C. After 10–50 min. the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times: DHT, 6.8–7.2 min.; androstanediol, 7.6–8.0 min.; T, 9.1–9.7 min.). The HPLC system consisted of a Waters Model 680 Gradient System equipped with a Hitachi Model 655α autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. The compound to be tested was pre-incubated with the enzyme (either 5α-reductase type 1 or 2) prior to initiation by addition of substrate testosterone. IC$_{50}$ values represent the concentration of inhibitor required to decrease enzyme conversion of testosterone to dihydrotestosterone by 50% of the control. IC$_{50}$ values were determined using a 6 point titration where the concentration of the inhibitor was varied from 0.1 to 1000 nM.

Representative compounds of formula I were tested in the above-described assay for 5α-reductase type 1 and type 2 inhibitory activity, and were found to have IC$_{50}$ values under 100 nM for inhibition of the type 1 isozyme. The tested compounds within the scope of formula I were at least about 100 times more active in the type 1 assay than in the type 2 assay, thereby demonstrating their utility as selective type 1 inhibitors.

A compound referred to herein as a 5α-reductase 2 inhibitor is a compound that shows inhibition of the 5α-reductase 2 isozyme in the above-described assay, having an IC$_{50}$ value of about or under 100 nM. A compound referred to herein as a dual 5α-reductase type 1 and 2 inhibitor is a compound that shows inhibition of the 5α-reductase type 1 and 2 isozymes in the above-described assay, having an IC$_{50}$ value of about or under 100 nM for each isozyme.

Human Dermal Papilla Cell Assay

The dermal papilla is a small group of cells at the base of each hair follicle, and it is presently thought that these cells are stem cells that form the basis for hair growth. These cells have been shown to have 5α reductase activity, and it is therefore possible to test inhibitors of 5α reductase in these cell culture systems.

Isolated and cultured dermal papilla cells are prepared according to the methods of Messenger, A. G., "The Culture of Dermal Papilla Cells From Human Hair Follicles," Br. *J. Dermatol.*, 110:685–689 (1984) and Itami, S. et al., "5α-Reductase Activity In Cultured Human Dermal Papilla Cells From Beard Compared With Reticular Dermal Fibroblasts," *J. Invest. Dermatol.*, 94:150–152 (1990). Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min. at 420 C. The pellets are resuspended in 20 mM Tris-HCl buffer, pH 7.5, at 420 C., containing 250 mM sucrose, 1 mM $MgCl_2$, and 2 mM $CaCl_2$, by vortexing and 10 passes through a 25-gauge needle. The crude homogenate is further homogenized by a teflonglass homogenizer, and is used as the cell homogenate. For the study of subcellular localization of 5α-reductase, the cell homogenate is centrifuged at 800×g for 10 min. to yield a crude nuclear pellet. The resultant supernatant is centrifuged at 10,000×g for 15 min. to produce a crude mitochondrial pellet. The supernatant is centrifuged at 100,000×g for 60 min. to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 ml of the cell homogenate, in a final volume of 100 ml. Each tube contains 50–100 mg of cellular protein. Incubation is carried out at 3720 C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et al., "Protein Measurement With The Folin Phenol Reagent," *J. Biol. Chem.*, 193:265–275 (1951).

After incubation, the reaction is stopped by adding 4 times volume of chloroform-methanol (2/1:V/V) containing 110 mg each of carrier steroids. The extracted steroids are analyzed by thin-layer chromatography as previously described by Gomez, et al., "In Vitro Metabolism Of Testosterone-4-$^{14}$C and D-androstene-3, 17-dione-4-$^{14}$C In Human Skin.,"*Biochem.*, 7:24–32 (1968), and the purity of each steroid is determined by the recrystallization method. The activity of 5α-reductase is expressed by the sum of dihydro-testosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

The following describes an example of methodology that can be used for detection of hair growth.

MICROPHOTOGRAPHY AND GLOBAL PHOTOGRAPHY PROCEDURE FOR DETECTION OF HAIR GROWTH

A. Macrophotographic Procedure
Location: ID card
 Haircount target area
Equipment: Film: Kodak-T-max 24 exposure each of same emulsion lot number
 Camera: Nikon N-6000
 Lens: Nikkor 60 mm f2.8
 Flashes: Nikon SB-21B Macroflash
 Device: registration device
 Photographic Procedure:
 In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly anterior to the center of the vertex bald spot, using a commercial tattooing machine or manually (needle and ink). An area approximately one square inch in size, centered at the tattoo at the leading edge of the balding area, is clipped short (~2mm). Cut hairs are removed from the area to be photographed, using tape. Compressed air and/or ethanol wipes may also be used to facilitate removal of cut hairs.
2. Magnification: Each lens supplied has a fixed reproduction ratio of 1:1.2.
 Aperture: Every photograph is taken at f/22.
 Film: T-Max 100 (24 exposure) is used.
3. Patient's haircount target area. Three exposures (–⅔, 0, and +⅔ f-stop).

A trained technician places a transparency over the photographic print and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and DeLong, E., *J. American Academy of Dermatology*, Vol. 23, p. 470 (1990).

B. Global Photographic Procedure
Locations: Color card/patient Id
 Global photograph
Equipment: Film: Kodachrome KR-64 24 exposure each of same emulsion lot number
Camera: Nikon N-6000
Lens: Nikkor 60 mm f2.8
Flashes: Nikon SB-23
 Photographic Procedure
 In these clinical photographs, the only variable allowed is the global area's appearance. Anything extraneous to the area (clothing, furniture, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.
2. Magnification: Each lens supplied has a fixed reproduction ratio of 1:6.
 Aperture: Every photograph will be taken at f/11.
 Film: Kodachrome (24 exposure) is used.
3. Patient's global photographs. Three exposures at zero compensation.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I

[Chemical structure I]

or a pharmaceutically acceptable salt thereof, wherein:
the C1–C2 bond designated "---" represents a single or double bond;
$R^1$ is selected from —H, methyl and ethyl;
$R^2$ is —H;
$R^3$ is —$OR^5$;
$R^5$ is independently selected at each occurrence from:
(a) —H,
(b) —$C_{1-10}$ straight or branched chain alkyl,
(c) —$C_{1-10}$ straight or branched chain alkyl substituted with 1 to 3 of phenyl, wherein each phenyl may independently be unsubstituted or substituted with 1 to 3 substituents selected from halo,
(d) an aryl group selected from phenyl, phenyl substituted with halo, naphthyl and biphenyl, and
(e) a heteroaryl group selected from pyridyl pyrrolyl, thienyl, furanyl, and quinolinyl.

2. The compound of claim 1 which is: 16β-(4-chlorophenoxy)-4-methyl-4aza-5α-19-norandrostan-3-one; and the pharmaceutically acceptable salts thereof.

3. The compound of claim 1 wherein the C1–C2 bond is a single bond and $R^1$ is —H or methyl.

4. The compound of claim 3 wherein $R^1$ is methyl; $R^2$ is —H; $R^3$ is $OR^5$; and $R^5$ is selected from:
(a) —$C_{1-10}$ straight or branched chain alkyl,
(b) —$C_{1-10}$ straight or branched chain alkyl substituted with 1 to 2 of phenyl, wherein each phenyl may independently be unsubstituted or substituted with 1 to 3 substituents selected from halo,
(c) an aryl group selected from phenyl, phenyl substituted with halo, naphthyl and biphenyl, and
(d) a heteroaryl group selected from pyridyl, pyrrolyl, thienyl, furanyl, and quinolinyl.

5. The compound 16β-(4-chlorophenoxy)-4-methyl-4-aza5α-19-norandrostan-3-one.

6. A pharmaceutical composition comprising a pharmaceutically acceptable carrier and 0.01 to 1000 mg per adult human per day of a compound of claim 1.

7. A pharmaceutical composition comprising a pharmaceutically acceptable carrier adapted for topical application and 0.01 to 1000 mg per adult human per day of a compound of claim 1.

8. A pharmaceutical composition comprising a pharmaceutically acceptable carrier adapted for oral administration and 0.01 to 1000 mg per adult human per day of a compound of claim 1.

* * * * *